(12) United States Patent
Jain et al.

(10) Patent No.: US 9,527,936 B2
(45) Date of Patent: Dec. 27, 2016

(54) POLYMER COMPRISING REPEAT UNITS WITH PHOTOACID-GENERATING FUNCTIONALITY AND BASE-SOLUBILITY-ENHANCING FUNCTIONALITY, AND ASSOCIATED PHOTORESIST COMPOSITION AND ELECTRONIC DEVICE FORMING METHOD

(71) Applicant: Rohm and Haas Electronic Materials LLC, Marlborough, MA (US)

(72) Inventors: Vipul Jain, North Grafton, MA (US); Paul J. LaBeaume, Auburn, MA (US); James W. Thackeray, Braintree, MA (US); James F. Cameron, Brookline, MA (US); Suzanne M. Coley, Mansfield, MA (US); Amy M. Kwok, Shrewsbury, MA (US); David A. Valeri, Leominster, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 14/833,245

(22) Filed: Aug. 24, 2015

(65) Prior Publication Data
US 2016/0102157 A1    Apr. 14, 2016

Related U.S. Application Data

(60) Provisional application No. 62/062,343, filed on Oct. 10, 2014.

(51) Int. Cl.
*G03F 7/004* (2006.01)
*C08F 22/10* (2006.01)
(Continued)

(52) U.S. Cl.
CPC ............. *C08F 22/10* (2013.01); *C07C 309/12* (2013.01); *C07C 381/12* (2013.01);
(Continued)

(58) Field of Classification Search
CPC ........ G03F 7/0045; G03F 7/0397; G03F 7/20; G03F 7/30; G03F 7/38; C07C 381/12; C07C 309/12; C08F 220/38; C08F 220/24; C08F 220/18; C08F 220/28; H01L 21/0274; H01L 21/0275
(Continued)

(56) References Cited

U.S. PATENT DOCUMENTS

| 5,130,392 A | 7/1992 | Schwalm et al. |
| 5,945,250 A | 8/1999 | Aoai et al. |

(Continued)

FOREIGN PATENT DOCUMENTS

JP    2013095880 A    5/2013

OTHER PUBLICATIONS

Liu et al., "Novel Polymeric Sulfonium Photacid Generator and Its Application for Chemically Amplified Photoresists" Proc. of SPIE vol. 9051 (2014) 905124-1-905124-8.

(Continued)

*Primary Examiner* — Amanda C Walke
(74) *Attorney, Agent, or Firm* — Cantor Colburn LLP

(57) ABSTRACT

A polymer includes repeat units, at least half of which are photoacid-generating repeat units. Each of the photoacid-generating repeat units includes photoacid-generating functionality and base-solubility-enhancing functionality. The polymer is useful as a component of a photoresist composition that further includes a second polymer that exhibits a change in solubility in an alkali developer under action of acid.

7 Claims, 4 Drawing Sheets

(51) Int. Cl.

| | |
|---|---|
| *C07C 309/12* | (2006.01) |
| *C07C 381/12* | (2006.01) |
| *C08F 220/18* | (2006.01) |
| *C08F 220/24* | (2006.01) |
| *C08F 220/28* | (2006.01) |
| *C08F 220/38* | (2006.01) |
| *G03F 7/039* | (2006.01) |
| *G03F 7/20* | (2006.01) |
| *G03F 7/38* | (2006.01) |
| *H01L 21/027* | (2006.01) |

(52) U.S. Cl.
CPC .......... *C08F 220/18* (2013.01); *C08F 220/24* (2013.01); *C08F 220/28* (2013.01); *C08F 220/38* (2013.01); *G03F 7/0045* (2013.01); *G03F 7/0046* (2013.01); *G03F 7/0397* (2013.01); *G03F 7/20* (2013.01); *G03F 7/38* (2013.01); *H01L 21/0274* (2013.01); *H01L 21/0275* (2013.01)

(58) Field of Classification Search
USPC .... 430/311, 270.1, 322, 325, 329, 330, 331; 526/243, 268, 245, 280
See application file for complete search history.

(56) References Cited

U.S. PATENT DOCUMENTS

| | | | |
|---|---|---|---|
| 8,927,191 B2 | 1/2015 | Tsuchiya et al. | |
| 8,945,814 B2 | 2/2015 | Cameron et al. | |
| 8,987,386 B2 | 3/2015 | Utsumi et al. | |
| 2008/0102407 A1* | 5/2008 | Ohsawa | C08F 20/22 430/286.1 |
| 2009/0233223 A1* | 9/2009 | Tachibana | G03F 7/0045 430/270.1 |
| 2009/0269696 A1* | 10/2009 | Ohsawa | C08F 220/18 430/270.1 |
| 2010/0055608 A1* | 3/2010 | Ohashi | C07D 493/18 430/270.1 |
| 2010/0099042 A1 | 4/2010 | Ohashi et al. | |
| 2011/0159429 A1 | 6/2011 | Thackeray et al. | |
| 2011/0269074 A1 | 11/2011 | Aqad et al. | |
| 2012/0129103 A1* | 5/2012 | Ohsawa | C07C 309/12 430/285.1 |
| 2012/0282551 A1 | 11/2012 | Matsuzawa et al. | |
| 2012/0322006 A1 | 12/2012 | Kato et al. | |
| 2013/0022911 A1 | 1/2013 | Utsumi et al. | |
| 2013/0065182 A1 | 3/2013 | Mori et al. | |
| 2013/0337378 A1* | 12/2013 | Ohashi | G03F 7/027 430/270.1 |
| 2014/0080062 A1 | 3/2014 | Thackeray et al. | |
| 2014/0186769 A1 | 7/2014 | Kaiho et al. | |
| 2014/0186770 A1 | 7/2014 | Aqad et al. | |
| 2015/0177615 A1 | 6/2015 | Jain et al. | |
| 2016/0002199 A1 | 1/2016 | Cameron et al. | |
| 2016/0070169 A1 | 3/2016 | Bozano et al. | |
| 2016/0102157 A1 | 4/2016 | Jain et al. | |
| 2016/0102158 A1 | 4/2016 | Labeaume et al. | |
| 2016/0103391 A1 | 4/2016 | Labeaume et al. | |
| 2016/0103392 A1 | 4/2016 | Labeaume et al. | |

OTHER PUBLICATIONS

Nakamura et al., "Photoresist Film Analysis to Investigate LWR Generation Mechanism" Proc. of SPIE vol. 8682 (2013) 86821H-1-86821H-13.

Oh et al., "The Noble Resists Composed of Cationic and Anionic Polymerizable PAGS" Proc. of SPIE vol. 7140 (2008) 714031-1-714031-9.

Satyanarayana et al, "Design and Synthesis of Novel Resist Materials for EUVL" Proc. of SPIE vol. 9049 (2014) 90481W-1-90481W-7.

Non-Final Office Action dated Feb. 25, 2016; U.S. Appl. No. 14/833,284, filed Aug. 24, 2015 (15 pages).

Non-Final Office Action dated Feb. 25, 2016; U.S. Appl. No. 14/833,278; filed Aug. 24, 2015 (14 pages).

Non-Final Office Action dated Jul. 28, 2016; U.S. Appl. No. 14/833,273, filed Aug. 24, 2015 (21 pages).

* cited by examiner

US 9,527,936 B2

POLYMER COMPRISING REPEAT UNITS WITH PHOTOACID-GENERATING FUNCTIONALITY AND BASE-SOLUBILITY-ENHANCING FUNCTIONALITY, AND ASSOCIATED PHOTORESIST COMPOSITION AND ELECTRONIC DEVICE FORMING METHOD

FIELD

The present invention relates to photoacid-generating polymers useful as components of photoresist compositions.

INTRODUCTION

As feature sizes of integrated circuits continue to shrink, next generation lithographic processes struggle to fit the stringent requirements to extend Moore's Law. It has long been recognized that increased photoacid generator (PAG) non-uniformity and acid diffusion have limited photoresist resolution, worsened line width roughness (LWR) (see, e.g., Nakamura et. al., Proc. SPIE 2013, 8682, 86821H-1), limited exposure latitude, and generally degraded photolithographic performance for chemically amplified resists. In the past, polymer-bound-PAG (PBP) systems have been implemented to increase PAG uniformity and control acid diffusion (see, e.g., Oh et. al., Proc. SPIE 2008, 7140 714031, pages 1-9; and U.S. Pat. No. 5,945,250 B2 to Aoai et al.). More recently, increased concentration of PAG in the matrix has been shown to further enhance lithographic performance, particularly when combined with a PBP system (U.S. Patent Application Publication No. US 2014/0080062 A1 of Thackeray et. al.). Despite these advances, there remains a need for photoresist compositions providing one or more of decreased critical dimension uniformity, decreased dose to clear energy, and increased contrast slope.

SUMMARY

One embodiment is a polymer comprising, based on 100 mole percent of total repeat units, 50 to 100 mole percent of photoacid-generating repeat units, wherein each of the photoacid-generating repeat units comprises (a) photoacid-generating functionality and (b) base-solubility-enhancing functionality selected from the group consisting of tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha,beta-fluorinated esters, polyalkyleneglycols, alpha-fluorinated alcohols, and combinations thereof.

Another embodiment is a photoresist composition comprising the polymer and a solvent.

Another embodiment is a method of forming an electronic device, comprising: (a) applying a layer of the photoresist composition on a substrate; (b) pattern-wise exposing the photoresist composition layer to activating radiation; and (c) developing the exposed photoresist composition layer to provide a resist relief image.

These and other embodiments are described in detail below.

DETAILED DESCRIPTION

Figure 1:
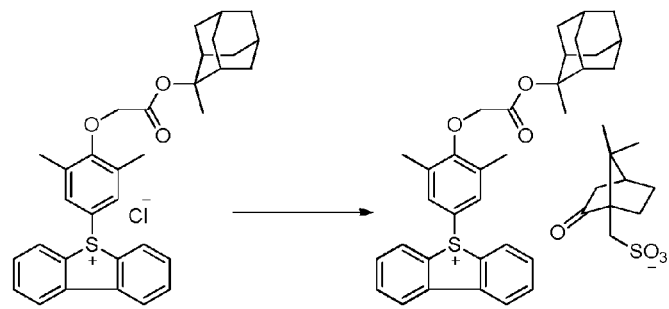
FIG. 1 is a synthetic scheme for the preparation of 5-(3,5-dimethyl-4-(2-(((1R,3S,5r,7r)-2-methyladamantan-2-yl)oxy)-2-oxoethoxy)phenyl)-5H-dibenzo[b,d]thiophen-5-ium((1S,4S)-7,7-dimethyl-2-oxobicyclo[2.2.1]heptan-1-yl)methanesulfonate.

The present inventors have determined that the photolithographic performance of a photoresist composition can be improved by the incorporation of a polymer that includes a majority of photoacid-generating repeat units, wherein each of the photoacid-generating repeat units comprises photoacid-generating functionality and base-solubility-enhancing functionality. The improvement in photolithographic performance can be manifested as one or more of decreased critical dimension uniformity, decreased dose to clear energy, and increased contrast slope.

Thus, one embodiment is a polymer comprising, based on 100 mole percent of total repeat units, 50 to 100 mole percent of photoacid-generating repeat units, wherein each of the photoacid-generating repeat units comprises (a) photoacid-generating functionality and (b) base-solubility-enhancing functionality selected from the group consisting of tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha,beta-fluorinated esters, polyalkyleneglycols, alpha-fluorinated alcohols, and combinations thereof. When a chemical group is characterized as unsubstituted or substituted, the "substituted" version thereof includes at least one substituent such as a halogen (i.e., F, Cl, Br, I), hydroxyl, amino, thiol, carboxyl, carboxylate, ester (including acrylates, methacrylates, and lactones), amide, nitrile, sulfide, disulfide, nitro, $C_{1-18}$ alkyl (including norbornyl and adamantyl), $C_{1-18}$ alkenyl (including norbornenyl), $C_{1-18}$ alkoxyl, $C_{2-18}$ alkenoxyl (including vinyl ether), $C_{6-18}$ aryl, $C_{6-18}$ aryloxyl, $C_{7-18}$ alkylaryl, or $C_{7-18}$ alkylaryloxyl. "Fluorinated" shall be understood to mean having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as in a 1,1-difluoroethyl group), three fluorine atoms (e.g., as in a 2,2,2-trifluoroethyl group), or fluorine atoms at each free valence of carbon (e.g., as in a perfluorinated group such as —$CF_3$, —$C_2F_5$, —$C_3F_7$, or —$C_4F_9$).

In some embodiments, the polymer comprises, based on 100 mole percent of total repeat units, 60 to 100 mole percent of photoacid-generating repeat units, specifically 70 to 100 mole percent of photoacid-generating repeat units, more specifically 80 to 100 mole percent of photoacid-generating repeat units, still more specifically 90 to 100 mole percent of photoacid-generating repeat units, even more specifically 95 to 100 mole percent of photoacid-generating repeat units. As used herein, the term "repeat unit" refers to divalent unit that is the residue of a polymerizable monomer. Conversely, "repeat unit" does not include monovalent groups, such as a terminal group derived from a polymerization initiator.

The photoacid-generating repeat units include photoacid-generating functionality. The photoacid-generating functionality can be chemically neutral, in the sense that it does not include an anion or a cation. Examples of chemically neutral photoacid-generating functionality include

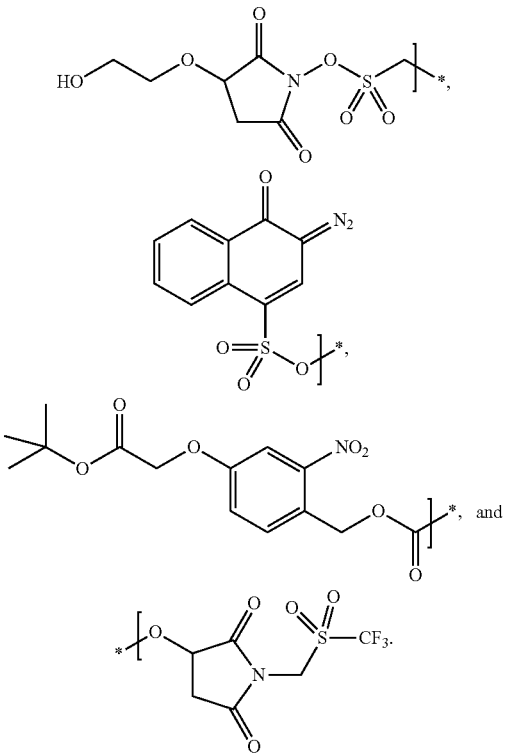

Although the examples shown above are monovalent, the photoacid-generating functionality can also be divalent, trivalent, or tetravalent, depending on the structure of the photoacid-generating repeat unit.

Alternatively, the photoacid-generating functionality can comprise a cation and an anion. For example, the cation can comprise a dihydrocarbyliodonium group or a trihydrocarbylsulfonium group. For example, the anion can comprise sulfonate (—$SO_3^-$), sulfonamidate (anion of sulfonamide; —$S(O)_2N^-R^3$, wherein $R^3$ is H or unsubstituted or substituted $C_{1-12}$ hydrocarbyl), or sulfonimidate (anion of sulfonimide; —$S(O)_2N^-S(O)_2R^3$, wherein $R^3$ is H or unsubstituted or substituted $C_{1-12}$ hydrocarbyl). As used herein, the term "hydrocarbyl", whether used by itself, or as a prefix, suffix, or fragment of another term, refers to a residue that contains only carbon and hydrogen unless it is specifically identified as "substituted hydrocarbyl". The hydrocarbyl residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. When the hydrocarbyl residue is described as substituted, it can contain heteroatoms in addition to carbon and hydrogen.

In addition to photoacid-generating functionality, each photoacid-generating repeat unit comprises base-solubility-enhancing functionality. Base-solubility-enhancing functionality includes functional groups that are base-soluble (e.g., polyalkyleneglycols, alpha-fluorinated alcohols); functional groups that are base-soluble after acid-catalyzed deprotection (e.g., tertiary esters, acetals, ketals, secondary carboxylic acid esters wherein the secondary carbon is substituted with at least one unsubstituted or substituted $C_{6-40}$ aryl); and functional groups that are base-soluble after base-catalyzed deprotection (e.g., fluorinated esters, lactones, sultones). Examples of base-solubility-enhancing functionality include tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha,beta-fluorinated esters, polyalkyleneglycols, alpha-fluorinated alcohols, and combinations thereof. In some embodiments, the base-solubility-enhancing functionality is a tertiary carboxylic acid ester, an acetal, a ketal, a lactone, or a combination thereof. In some embodiments, base-solubility-enhancing functionality resides in the photoacid-generating cation.

In some embodiments, the photoacid-generating repeat unit comprises a polymer-bound anion and a non-polymer-bound cation. For example, the photoacid-generating repeat units can have the structure

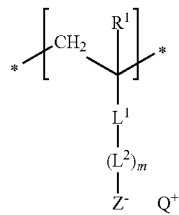

wherein $R^1$ is independently in each of the repeat units H, F, —CN, $C_{1-10}$ alkyl, or $C_{1-10}$ fluoroalkyl; $L^1$ is independently in each of the repeat units —O—, —C(O)—O—, unsubstituted $C_{6-18}$ arylene, or substituted $C_{6-18}$ arylene; m is independently in each of the repeat units 0 or 1; $L^2$ is independently in each of the repeat units an unsubstituted or substituted $C_{1-20}$ hydrocarbylene, wherein the substituted $C_{1-20}$ hydrocarbylene can, optionally, include one or more in-chain divalent heteroatom-containing groups such as —O—, —S—, —$NR^2$—, —$PR^2$—, —C(O)—, —OC(O)—, —C(O)O—, —OC(O)O—, —$N(R^2)C(O)$—, —$C(O)N(R^2)$—, —$OC(O)N(R^2)$—, —$N(R^2)C(O)O$—, —S(O)—, —$S(O)_2$—, —$N(R^2)S(O)_2$—, —$S(O)_2N(R^2)$—, —$OS(O)_2$—, or —$S(O)_2O$—, wherein $R^2$ is H or $C_{1-12}$ hydrocarbyl; $Z^-$ is independently in each of the repeat units sulfonate (—$SO_3^-$), sulfonamidate (anion of sulfonamide; —$S(O)_2N^-R^3$, wherein $R^3$ is H or unsubstituted or substituted $C_{1-12}$ hydrocarbyl), or sulfonimidate (anion of sulfonimide; —$S(O)_2N^-S(O)_2R^3$, wherein $R^3$ is H or unsubstituted or substituted $C_{1-12}$ hydrocarbyl); and $Q^+$ is photoacid-generating cation; wherein at least one of $L^1$, $L^2$ (when m is 1), and $Q^+$ comprises the base-solubility-enhancing functionality. In other words, if m is zero, then at least one of $L^1$ and $Q^+$ comprises base-solubility-enhancing functionality, and if m is one, then at least one of $L^1$, $L^2$, and $Q^+$ comprises base-solubility-enhancing functionality.

In specific embodiments of the photoacid-generating repeat unit comprising a polymer-bound anion and a non-polymer-bound cation, $R^1$ is independently in each of the repeat units H or methyl; $L^1$ is —C(O)—O— in each of the repeat units; m is 1 in each of the repeat units; $L^2$ is independently in each of the repeat units a fluorine-substituted $C_{2-20}$ hydrocarbylene, wherein the fluorine-substituted $C_{2-20}$ hydrocarbylene can, optionally, include one or more in-chain divalent heteroatom-containing groups that is —O—, —OC(O)—, or —C(O)O—; $Z^-$ is sulfonate (—$SO_3^-$) in each of the repeat units; and $Q^+$ is independently in each of the repeat units an unsubstituted or substituted tri($C_{1-60}$-hydrocarbyl)sulfonium ion, or an unsubstituted or substituted di($C_{1-60}$-hydrocarbyl)iodonium ion. When $R^1$ is H and $L^1$ is —C(O)—O—, then the repeat unit is an acrylate ester. When $R^1$ is methyl and $L^1$ is —C(O)—O—, then the repeat unit is a methacrylate ester.

In some embodiments, the photoacid-generating functionality comprises a polymer-bound cation and a non-polymer-bound anion. For example the photoacid-generating repeat units have the structure

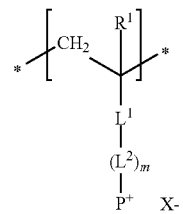

wherein $R^1$ is independently in each of the repeat units H, F, —CN, $C_{1-10}$ alkyl, or $C_{1-10}$ fluoroalkyl; $L^1$ is independently in each of the repeat units —O—, —C(O)—O—, unsubstituted $C_{6-18}$ arylene, or substituted $C_{6-18}$ arylene; m is independently in each of the repeat units 0 or 1; $L^2$ is independently in each of the repeat units an unsubstituted or substituted $C_{1-20}$ hydrocarbylene, wherein the substituted $C_{1-20}$ hydrocarbylene can, optionally, include one or more in-chain divalent heteroatom-containing groups that is —O—, —S—, —$NR^2$—, —$PR^2$—, —C(O)—, —OC(O)—, —C(O)O—, —OC(O)O—, —$N(R^2)C(O)$—, —$C(O)N(R^2)$—, —$OC(O)N(R^2)$—, —$N(R^2)C(O)O$—, —S(O)—, —$S(O)_2$—, —$N(R^2)S(O)_2$—, —$S(O)_2N(R^2)$—, —$OS(O)_2$—, or —$S(O)_2O$—, wherein $R^2$ is H or $C_{1-12}$ hydrocarbyl; $P^+$ is independently in each of the repeat units a monovalent group comprising an unsubstituted or substituted tri($C_{1-60}$-hydrocarbyl)sulfonium ion, or an unsubstituted or substituted di($C_{1-60}$-hydrocarbyl)iodonium ion; and $X^-$ is a monovalent anion; wherein at least one of $L^1$, $L^2$ (when m is 1), and $Q^+$ comprises the base-solubility-enhancing functionality.

In specific embodiments of the photoacid-generating repeat unit comprising a polymer-bound cation and a non-polymer-bound anion, $R^1$ is independently in each of the repeat units H or methyl; $L^1$ is —C(O)—O— in each of the repeat units; $P^+$ is independently in each of the repeat units a monovalent group comprising an unsubstituted or substituted tri($C_{1-60}$-hydrocarbyl)sulfonium ion; and $X^-$ comprises sulfonate (—$SO_3^-$) in each of the repeat units. When $R^1$ is H and $L^1$ is —C(O)—O—, then the repeat unit is an acrylate ester. When $R^1$ is methyl and $L^1$ is —C(O)—O—, then the repeat unit is a methacrylate ester.

In some embodiments of the polymer, the photoacid-generating repeat units are derived from a single monomer. Alternatively, the photoacid-generating repeat units can be derived from at least two different monomers.

The polymer comprises 50 to 100 mole percent of photoacid-generating repeat units, based on 100 mole percent of total repeat units. When the polymer comprises less than 100 mole percent of photoacid generating repeat units, the other repeat units can comprise photoacid-generating functionality or not, and they can comprise base-solubility-enhancing functionality or not. Examples of monomers from which such other repeat units can be derived are

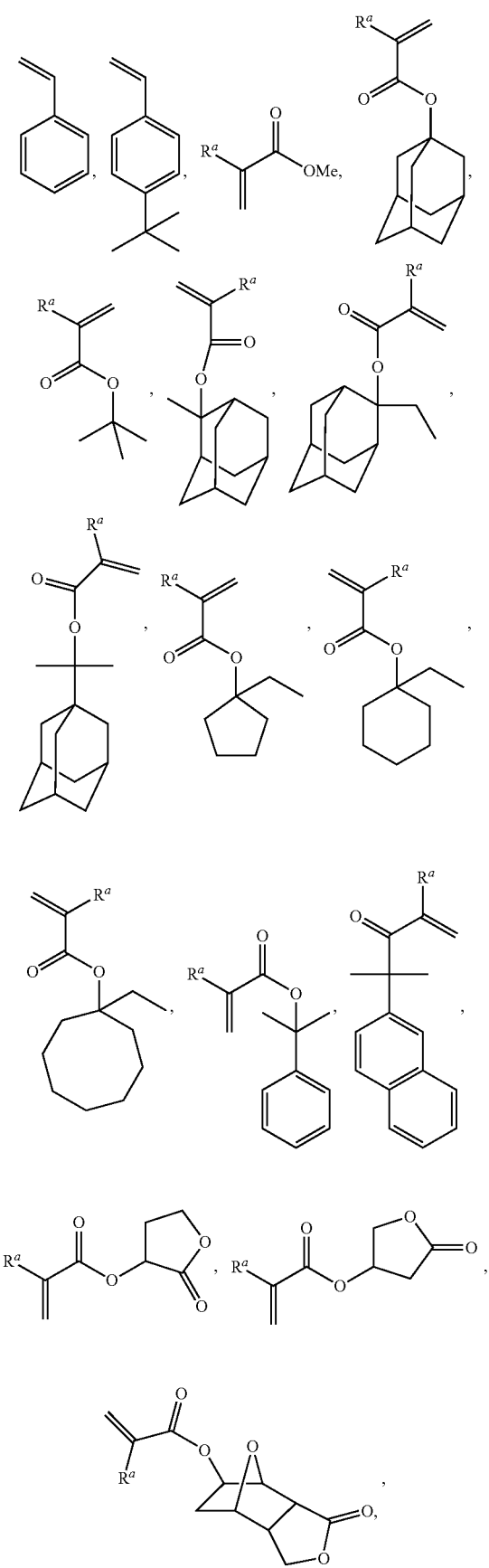
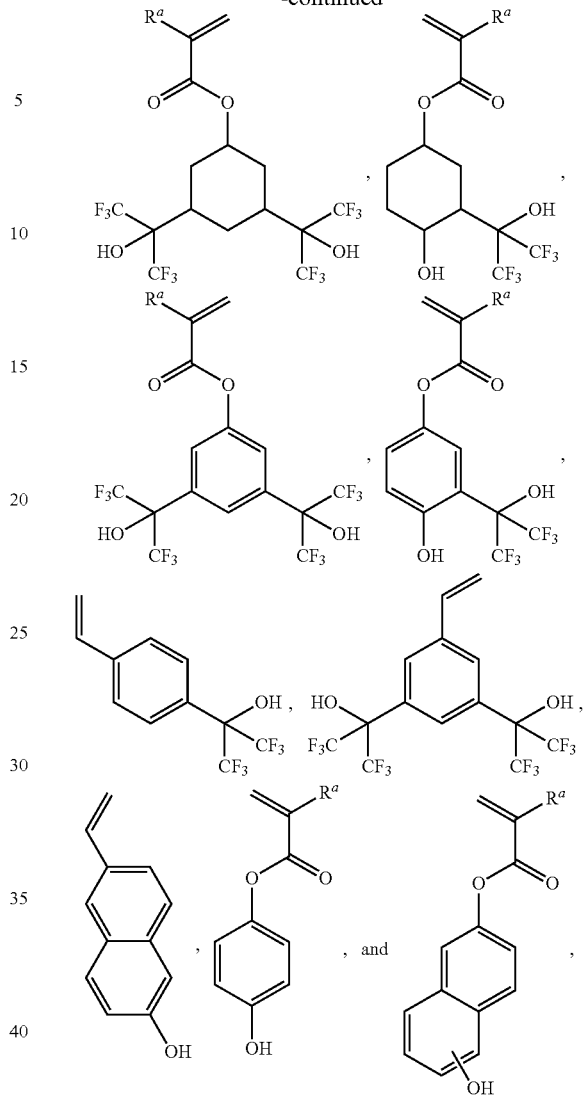

wherein each occurrence of $R^a$ is independently H, F, —CN, $C_{1-10}$ alkyl, or $C_{1-10}$ fluoroalkyl.

In some embodiments, the polymer has a weight average molecular weight of 2,500 to 10,000 daltons, specifically 3,000 to 7,000 daltons.

Another embodiment is a photoresist composition comprising the polymer and a solvent. Any of the variations described above in the context of the polymer apply as well to the photoresist composition comprising the polymer. Suitable solvents include anisole; esters including ethyl lactate, methyl 2-hydroxybutyrate (HBM), n-butyl acetate, 1-methoxy-2-propyl acetate (also referred to as propylene glycol methyl ether acetate, PGMEA), methoxyethyl propionate, ethoxyethyl propionate, and gamma-butyrolactone; alcohols including 1-methoxy-2-propanol (also referred to as propylene glycol methyl ether, PGME), and 1-ethoxy-2 propanol; ketones including cyclohexanone and 2-heptanone; and combinations thereof.

Another embodiment is a method of forming an electronic device, comprising: (a) applying a layer of the photoresist composition on a substrate; (b) pattern-wise exposing the photoresist composition layer to activating radiation; and (c) developing the exposed photoresist composition layer to provide a resist relief image.

The invention is further illustrated by the following examples.

Example 1

FIG. 1 is a synthetic scheme for the preparation of 5-(3,5-dimethyl-4-(2-(((1R,3S,5r,7r)-2-methyladamantan-2-yl)oxy)-2-oxoethoxy)phenyl)-5H-dibenzo[b,d]thiophen-5-ium((1S,4S)-7,7-dimethyl-2-oxobicyclo[2.2.1]heptan-1-yl)methanesulfonate.

5-(3,5-Dimethyl-4-(2-(((1R,3S,5r,7r)-2-methyladamantan-2-yl)oxy)-2-oxoethoxy)phenyl)-5H-dibenzo[b,d]thiophen-5-ium((1S,4S)-7,7-dimethyl-2-oxobicyclo[2.2.1]heptan-1-yl)methanesulfonate 5-(3,5-dimethyl-4-(2-(((1R,3S,5r,7r)-2-methyladamantan-2-yl)oxy)-2-oxo ethoxy)phenyl)-5H-dibenzo[b,d]thiophen-5-ium((1S,4S)-7,7-dimethyl-2-oxobicyclo[2.2.1]heptan-1-yl)methanesulfonate chloride (19.4 g, 35.6 mmol) and sodium camphorsulfonate (9.52 g, 37.4 mmol) were dissolved in dichloromethane (200 mL) and water (200 mL) and stirred at room temperature overnight. The layers were separated and the organic phase washed with water (6×150 mL) and concentrated. The crude solid was dissolved in minimal dichloromethane, precipitated into methyl tert-butyl ether (500 mL), filtered and dried to afford the title compound (19.0 g, 72%) as a white solid. $^1$H NMR (500 MHz, $(CD_3)_2CO$) δ: 8.52 (d, J=7.8 Hz, 2H), 8.33 (d, J=7.8 Hz, 2H), 7.97 (dt, J=8.4, 0.9 Hz, 2H), 7.76 (dt, J=8.1, 0.9 Hz, 2H), 7.32 (s, 2H), 4.56 (s, 2H), 2.86 (d, J=17.7 Hz, 1H), 2.72 (t, J=7.5 Hz, 1H), 2.35 (d, J=17.7 Hz, 1H), 2.22 (s, 6H), 2.13-2.28 (m, 2H), 1.44-1.97 (m, 26H), 1.26 (d, J=9 Hz, 1H).

Example 2

Figure 2:
FIG. 2 is a synthetic scheme for the preparation of 2-(2-methoxyethoxy)ethyl 4-tosylate.

FIG. 2 is a synthetic scheme for the preparation of 2-(2-methoxyethoxy)ethyl 4-tosylate.

2-(2-Methoxyethoxy)ethyl 4-tosylate

Sodium hydroxide (62 g, 1.55 mol) in water (350 mL) was carefully added in one portion to 2-(2-methoxyethoxy)ethanol (110 g, 912 mmol) in tetrahydrofuran (350 mL) at 0° C. under vigorous stirring and stirred for 5 min. Then tosyl chloride (209 g, 1.09 mol) in tetrahydrofuran (350 mL) was added over 10 minutes, warmed to room temperature and stirred for 4 h. The reaction mixture was diluted with water (350 mL) and extracted with methyl tert-butyl ether (2×700 mL). The combined organic layers were washed with 1M aqueous sodium hydroxide (2×500 mL), water (3×500 mL), dried over sodium sulfonate and concentrated to afford the title compound (221 g, 88%) as a clear oil. $^1$H NMR (500 MHz, $(CD_3)_2CO$) δ: 7.81 (d, J=8.0 Hz, 2H), 7.49 (d, J=8.0 Hz, 2H), 4.14-4.19 (m, 2H), 3.63-3.68 (m, 2H), 3.49-3.53 (m, 2H), 3.39-3.44 (m, 2H), 3.26 (s, 3H), 3.47 (s, 3H).

Example 3

Figure 3:
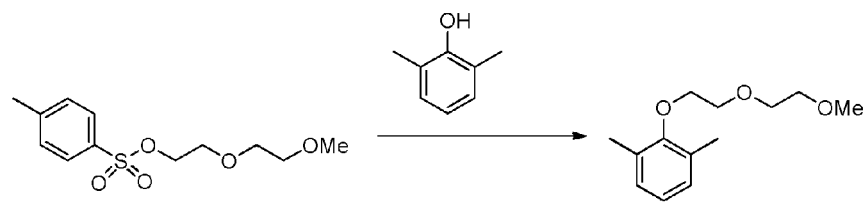
FIG. 3 is a synthetic scheme for the preparation of 2-(2-(2-methoxyethoxy)ethoxy)-1,3-dimethylbenzene.

FIG. 3 is a synthetic scheme for the preparation of 2-(2-(2-methoxyethoxy)ethoxy)-1,3-dimethylbenzene.

2-(2-(2-Methoxyethoxy)ethoxy)-1,3-dimethylbenzene

Dimethylformamide (200 mL) was added to sodium hydride (18 g as 60 weight percent in oil, 450 mmol) under nitrogen. Next, 2,6-dimethylphenol (50 g, 409 mmol) in dimethylformamide (100 mL) was added drop-wise and heated to 50° C. where 2-(2-methoxyethoxy)ethyl 4-tosylate (113 g, 413 mmol) in dimethylformamide (200 mL) was added drop-wise and stirred overnight. The reaction mixture was diluted with methyl tert-butyl ether (1 L) and washed with water (1 L). The water layer was back extracted with methyl tert-butyl ether (500 mL) and the combined organics washed with 1M potassium hydroxide (3×300 mL), hydrochloric acid (1 weight percent, 2×500 mL), water (2×500 mL), brine (1×250 mL), dried over sodium sulfate and concentrated to afford the title compound (90.5 g, 90%) as a clear oil. $^1$H NMR (300 MHz, $(CD_3)_2CO$) δ: 6.99 (d, J=7.8 Hz, 2H), 6.88 (t, J=7.8 Hz, 1H), 3.90-3.94 (m, 2H), 3.75-3.80 (m, 2H), 3.64-3.68 (m, 2H), 3.50-3.54 (m, 2H), 3.31 (s, 3H), 2.26 (s, 6H).

Example 4

Figure 4:
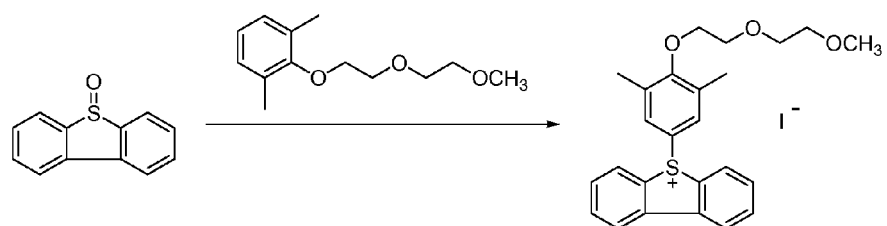
FIG. 4 is a synthetic scheme for the preparation of 5-(4-(2-(2-methoxyethoxy)ethoxy)-3,5-dimethylphenyl)-dibenzothiophen-5-ium iodide.

FIG. 4 is a synthetic scheme for the preparation of 5-(4-(2-(2-methoxyethoxy)ethoxy)-3,5-dimethylphenyl)-dibenzothiophen-5-ium iodide.

5-(4-(2-(2-Methoxyethoxy)ethoxy)-3,5-dimethylphenyl)-dibenzothiophen-5-ium iodide Eaton's Reagent (60 mL) was added to a solution of dibenzothiophene oxide (20.0 g, 0.1 mol) and 2-(2-(2-methoxyethoxy)ethoxy)-1,3-dimethylbenzene (24.7 g, 0.11 mol) in dichloromethane (60 mL) at 0° C., warmed to room temperature and stirred overnight. The reaction mixture was cooled to 0° C. and slowly quenched by the addition of water (300 mL) and washed with methyl tert-butyl ether (2×250 mL). The organic layer is discarded and sodium iodide (30 g, 0.200 mmol) in water (100 mL) was added to the aqueous layer under vigorous stirring. The precipitate was filtered and washed with copious amounts of water, suspended in minimal acetone, stirred at room temperature for 1 hour and filtered to afford the title compound (30.2 g, 57%) as an off-white solid. $^1$H NMR (500 MHz, $(CD_3)_2SO$) δ: 8.52 (d, J=8.0 Hz, 2H), 8.33 (d, J=8.0 Hz, 2H), 7.96 (t, J=7.5 Hz, 2H), 7.75 (d, J=7.5 Hz, 2H), 7.31 (s, 2H), 3.94 (vis t, J=5.5 Hz, 2H), 3.67 (vis t, J=5.0 Hz, 2H), 3.55 (vis t, 6.0 Hz, 2H), 3.42 (vis t, J=4.5 Hz, 2H), 3.21 (s, 3H), 2.20 (s, 6H).

Example 5

Figure 5:
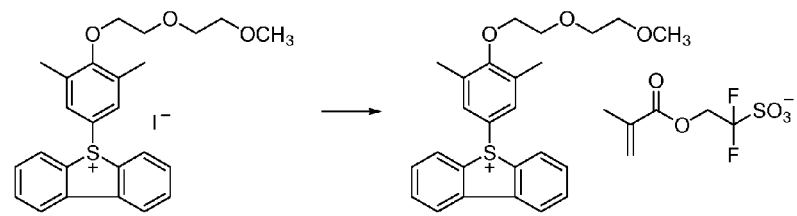
FIG. 5 is a synthetic scheme for the preparation of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate.

FIG. 5 is a synthetic scheme for the preparation of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate.

5-(4-(2-(2-Methoxyethoxy)ethoxy)-3,5-dimethylphenyl)-5H-dibenzo[b,d]thiophen-5-ium 1,1-difluoro-2-(methacryloyloxy)ethanesulfonate 5-(4-(2-(2-methoxyethoxy)ethoxy)-3,5-dimethylphenyl)-dibenzothiophen-5-ium iodide (13.0 g, 24.3 mmol) and triethylammonium 1,1-difluoro-2-(methacryloyloxy)ethanesulfonate (8.22 g, 24.8 mmol) were dissolved in dichloromethane (150 mL) and water (150 mL) and stirred at room temperature overnight. The layers were separated and the organic layer was washed with water (8×150 mL) and concentrated under reduced pressure to afford the title compound (15.1 g, 97%) as a white hygroscopic solid which was stored under inert nitrogen atmosphere. $^1$H NMR (500 MHz, $(CD_3)_2CO$) δ: 8.52 (d, J=8.0 Hz, 2H), 8.38 (d, J=8.5 Hz, 2H), 8.00 (t, J=7.5 Hz, 2H), 7.80 (t, J=8.0 Hz, 2H), 7.51

(s, 2H), 6.13-6.16 (m, 1H), 5.67-5.69 (m, 1H), 4.77 t, J=15.5 Hz, 2H), 4.02-4.05 (m, 2H0, 3.73-3.77 (m, 2H), 3.58-3.62 (m, 2H), 3.44-3.49 (m, 2H), 3.25 (s, 3H), 2.26 (s, 6H), 1.13 (s, 3H).

Example 6

Figure 6:
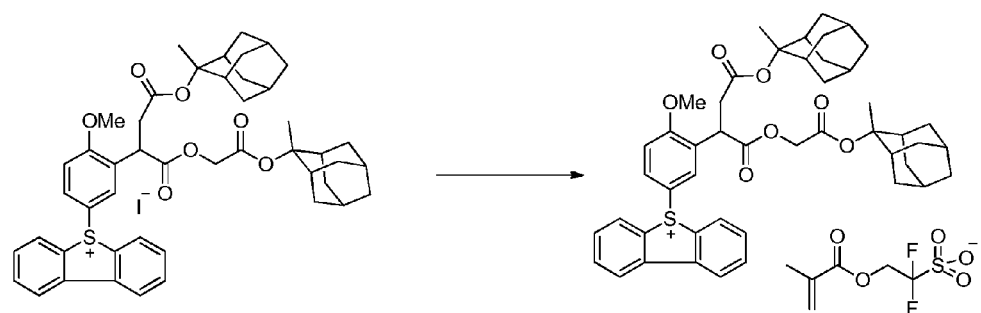
FIG. 6 is a synthetic scheme for the preparation of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

FIG. 6 is a synthetic scheme for the preparation of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

5-(4-Methoxy-3-(4-((2-methyladamantan-2-yl)oxy)-1-(2-(((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (37.8 g, 47.4 mmol and N,N,N-trimethyl-1-phenylmethanaminium 1,1-difluoro-2-(methacryloyloxy)ethanesulfonate (18.9 g, 49.8 mmol) were dissolved in DCM (250 mL) and water (250 mL) and stirred at 25° C. overnight. The layers were separated, the aqueous phase extracted with dichloromethane (100 mL), the combined organic layers washed with water (8×200 mL) and concentrated under reduced pressure to afford the title compound (36.0, 77%) as an off white solid. $^1$H NMR (500 MHz, (CD$_3$)$_2$CO) δ: (8.52-8.56 (m, 2H), 8.37 (d, J=8 Hz, 1H), 8.31 (d, J=8.5 Hz, 1H), 7.99-8.06 (m, 2H), 7.78-7.85 (m, 3H), 7.63 (dd, J=9, 1.5 Hz, 1H), 7.31 (d, J=9 Hz, 1H), 6.16-6.19 (m, 1H), 5.64-6.69 (m, 1H), 5.62 (s, 2h), 4.72-4.79 (m, 2H), 4.50-4.65 (m, 2H), 4.42-4.47 (m, 1H), 3.96 (s, 3H), 2.99-3.07 (m, 1H), 2.63-2.70 (m, 1H), 2.10-2.30 (m, 4H), (1.42-2.09 (m, 31H).

Example 7

Figure 7:
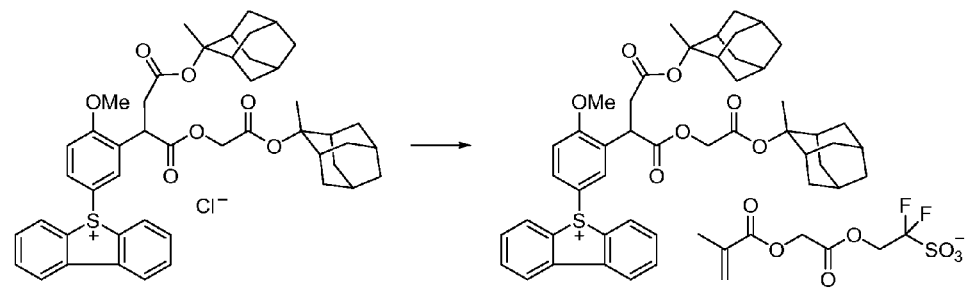
FIG. 7 is a synthetic scheme for the preparation of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

FIG. 7 is a synthetic scheme for the preparation of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

5-(4-Methoxy-3-(4-(((1R,3S,5r,7r)-2-methyladamantan-2-yl)oxy)-1-(2-(41R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (40.0 g, 50.2 mmol) and N,N,N-trimethyl-1-phenylmethanaminium 1,1-difluoro-2-(2-(methacryloyloxy)acetoxy)ethanesulfonate (23.0 g, 52.6 mmol) were dissolved in dichloromethane (300 mL) and water (300 mL) and stirred at room temperature overnight. The layers were separated, the organic phase washed with water (7×250 mL) and concentrated to afford the title compound (43.4 g, 83%) as a white solid. $^1$H NMR (300 MHz, (CD$_3$)$_2$SO) δ: 8.52 (d, J=7.8 Hz, 2H), 8.31 (d, J=8.1 Hz, 1H), 8.26 (d, J=8.1 Hz, 1H), 7.97 (t, J=7.8 Hz, 2H), 7.75 (t, J=7.8 Hz, 1H), 7.71 (d, J=2.4 Hz, 1H), 7.35 (dd, J=9.0, 2.4 Hz, 1H), 7.22 (d, J=9.0 Hz, 1H), 6.12-6.17 (m, 1H), 5.76-5.82 (m, 1H), 4.87 (s, 2H), 4.63 (t, J=15.6 Hz, 2H), 4.59 (s, 2H), 4.35 (t, J=7.5 Hz, 1H), 3.82 (s, 3H), 2.92-3.10 (m, 2H), 2.56-2.68 (m, 1H), 1.35-2.25 (m, 36H).

Example 8

Figure 8:
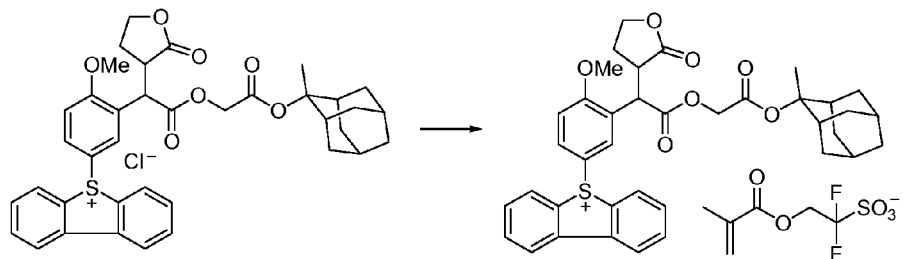
FIG. 8 is a synthetic scheme for the preparation of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

FIG. 8 is a synthetic scheme for the preparation of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

5-(4-Methoxy-3-(2-(2-(41R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate 5-(4-methoxy-3-(2-(2-(((1R,3S,5r,7r)-2-methyladamantan-2-yl)oxy)-2-oxoethoxy)-2-oxotetrahydrofuran-3-yl)ethyl)phenyl)-5H-dibenzo[b,d]thiophen-5-ium chloride (40.0 g, 59.2 mmol) and N,N,N-trimethyl-1-phenylmethanaminium 1,1-difluoro-2-(methacryloyloxy)ethanesulfonate (23.6 g, 62.2 mmol) were dissolved in dichloromethane (300 mL) and water (300 mL) and stirred at room temperature overnight. The layers were separated, the organic phase washed with water (7×250 mL), concentrated to half volume and precipitated into methyl tert-butyl ether (1.5 L). The precipitate was filtered, washed with methyl tert-butyl ether (2×500 mL) and dried to afford the title compound (39.1 g, 76%) as a white solid. $^1$H NMR (300 MHz, (CD$_3$)$_2$SO) δ: 8.53 (d, J=7.8 Hz, 2H), 8.34 (d, J=8.1 Hz, 2H), 8.27 (d, J=7.8 Hz, 2H), 7.97 (t, J=7.5 Hz, 2H), 7.75 (dt, J=7.8, 2.7 Hz, 1H), 7.68 (d, J=1.8 Hz, 1H), 7.38 (dd, J=9.0, 2.1 Hz, 1H), 7.23 (d, J=9.0 Hz, 1H), 6.12 (vis s, 1H), 5.77 (vis s, 1H), 4.64 (t, J=15.6 Hz, 2H), 4.60 (s, 2H), 4.25 (d, J=7.2 Hz, 1H), 4.05-4.21 (m, 2H), 3.82 (s, 3H), 3.36-3.51 (m, 2H), 2.14-2.20 (m, 1H), 1.38-2.04 (m, 17H).

Example 9

In general polymer molecular weight were determined from $^{13}$C NMR spectra obtained on a Varian 300 Megahertz NMR spectrometer operating with a relaxation delay of 2 seconds by integration of initiator end groups and one of the carbons of the PAG unit.

Figure 9:
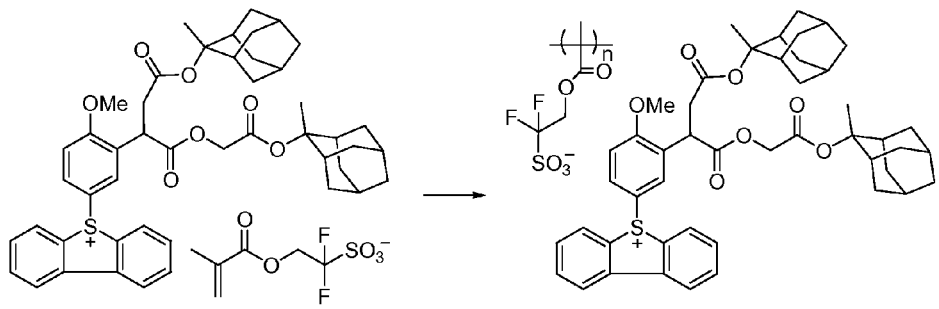
FIG. 9 is a synthetic scheme for the preparation of a homopolymer of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

FIG. 9 is a synthetic scheme for the preparation of a homopolymer of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

Homopolymer of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate (10.0 g, 10.2 mmol) was dissolved in ethyl lactate/gamma-butyrolactone (3/7 v/v, 15.0 g). The initiator 2,2'-azobis(2.4-dimethyl valeronitrile) (1.00 g) was dissolved in acetonitrile/tetrahydrofuran (2/1 v/v, 1.00 g). The monomer and initiator solutions were added drop-wise over 4 hours to a flask preheated to 80° C.

followed by an initiator chase. The reaction mixture was stirred for 2 hours, cooled to room temperature, diluted with methanol (17 g) and precipitated into diisopropyl ether (800 g). The polymer was filtered and dried to afford the title compound (8.00 g, 80%, weight average molecular weight 3,972 daltons) as a white solid.

Example 10

Figure 10:
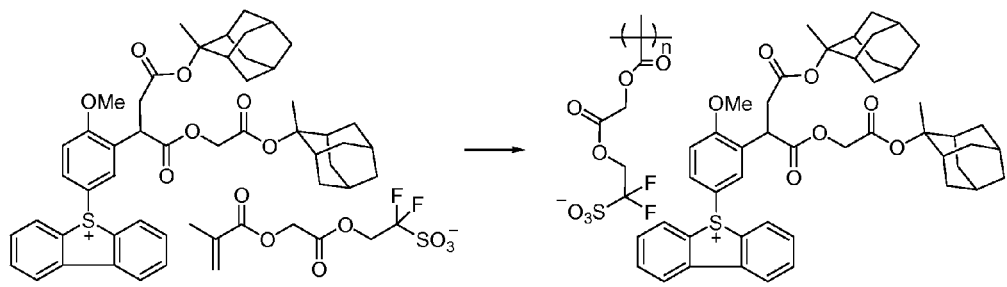
FIG. 10 is a synthetic scheme for the preparation of a homopolymer of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

FIG. 10 is a synthetic scheme for the preparation of a homopolymer of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

Homopolymer of 5-(4-methoxy-3-(4-(((1R,3S,5r,7r)-2-methyladamantan-2-yl)oxy)-1-(2-(41R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate (1.00 g, 0.953 mmol) was dissolved in ethyl lactate/gamma-butyrolactone (3/7 v/v, 1.50 g). 2,2'-Azobis(2.4-dimethyl valeronitrile) (0.150 g) was dissolved in acetonitrile/tetrahydrofuran (2/1 v/v, 0.150 g). The monomer and initiator solutions were added drop-wise to a flask preheated to 75° C. and stirred for 8 h. The reaction mixture was cooled to room temperature, diluted with acetone (0.900 g) and precipitated as a sticky solid from acetone/diisopropylether (1:1 25.0 g), decanted, redissolved in acetone (2.40 g) and methanol (0.500 g) and precipitated into diisopropyl ether (20× reaction volume). The polymer was filtered and dried to afford the title compound (0.550 g, 55%, weight average molecular weight 3,000 daltons) as a white solid.

Example 11

Figure 11:
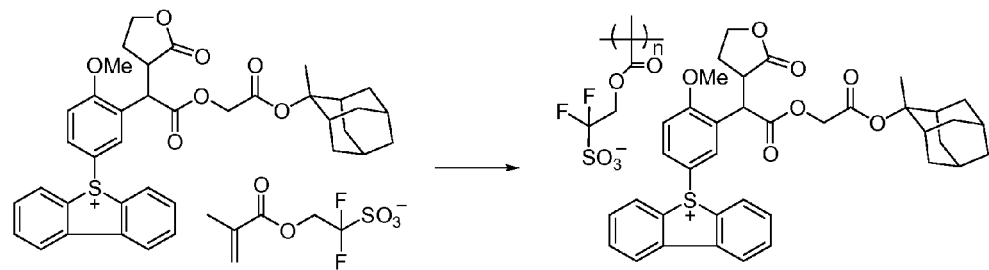
FIG. 11 is a synthetic scheme for the preparation of a homopolymer of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

FIG. 11 is a synthetic scheme for the preparation of a homopolymer of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

Homopolymer of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate (15.0 g, 17.3 mmol) was dissolved in ethyl lactate/gamma-butyrolactone (3/7 v/v, 60.0 g). 2,2'-Azobis(2.4-dimethyl valeronitrile) (2.25 g) was dissolved in acetonitrile/tetrahydrofuran (2/1 v/v, 2.25 g). The monomer and initiator solutions were added drop-wise over 4 hours to a flask preheated to 90° C. The reaction mixture was cooled to room temperature, diluted with tetrahydrofuran (10× reaction volume) and acetone (5× reaction volume) and precipitated into diisopropyl ether (2000 g). The polymer was filtered and dried to afford the title compound (7.96 g, 53%, weight average molecular weight 3,476 daltons) as a white solid.

Example 12

Figure 12:
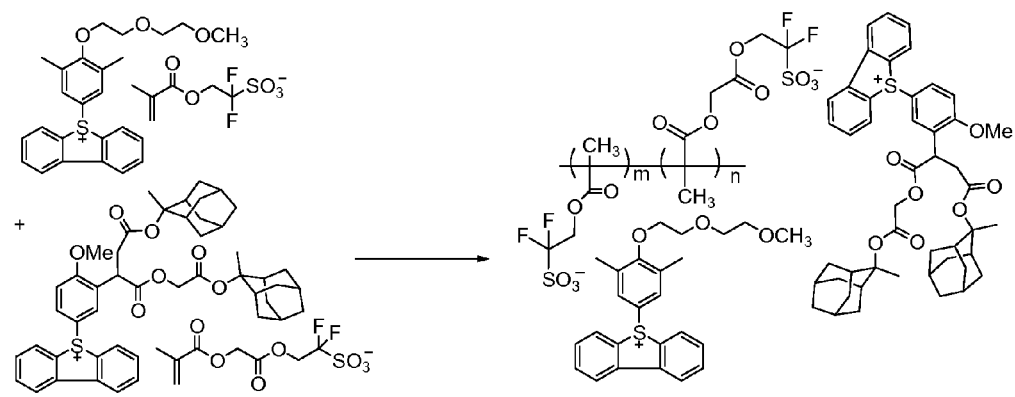
FIG. 12 is a synthetic scheme for the preparation of a copolymer of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

FIG. 12 is a synthetic scheme for the preparation of a copolymer of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

Copolymer of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate (3.00 g, 8.25 mmol) and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate (7.00 g, 6.67 mmol) were dissolved in ethyl lactate/gamma-butyrolactone (3/7 v/v, 15.0 g). 2,2'-Azobis(2.4-dimethyl valeronitrile) (1.50 g) was dissolved in acetonitrile/tetrahydrofuran (2/1 v/v, 1.50 g). The monomer and initiator solutions were added drop-wise to a flask preheated to 75° C. over 4 hours. The reaction mixture was cooled to room temperature, precipitated as a sticky solid from methanol/diisopropyl ether (1:1, 20× reaction volume), redissolved into acetone (20.0 mL) and methanol (0.300 g) and reprecipitated from diisopropyl ether/methanol (19:1 v/v, 2000 mL), filtered and dried to afford the title compound (6.00 g, 60%, weight average molecular weight 2,500 daltons) as a white solid.

Example 13

Figure 13:
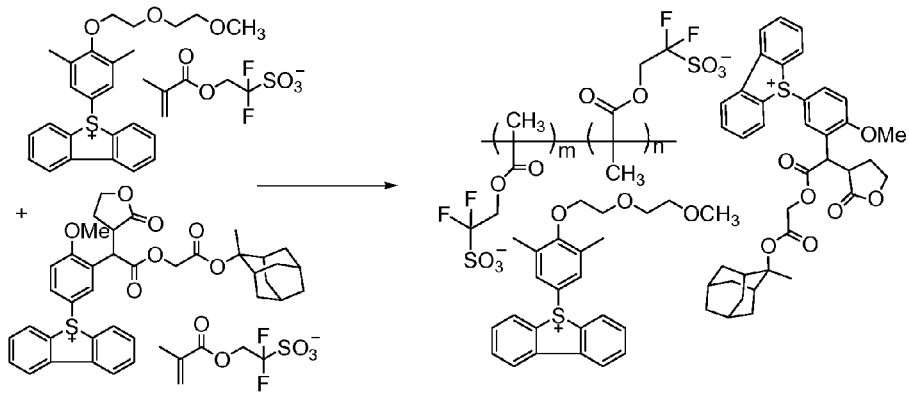
FIG. 13 is a synthetic scheme for the preparation of a copolymer 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

FIG. 13 is a synthetic scheme for the preparation of a copolymer 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

Copolymer 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate (4.50 g, 12.4 mmol) and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl) ethyl)phenyl)-5H-dibenzo[b,d]thiophen-5-ium 1,1-difluoro-2-(methacryloyloxy)ethanesulfonate (10.5 g, 12.1 mmol) were dissolved in ethyl lactate/gamma-butyrolactone (3/7 v/v, 60.0 g). 2,2'-Azobis(2.4-dimethyl valeronitrile) (2.25 g) was dissolved in acetonitrile/tetrahydrofuran (2/1 v/v, 2.25 g). The monomer and initiator solutions were added dropwise to a flask preheated to 75° C. over 4 h. The reaction mixture was cooled to room temperature, diluted with tetrahydrofuran (5× reaction volume) and acetone (5× reaction volume), precipitated from diisopropyl ether (20× reaction volume), filtered and dried to afford the title compound (11.0 g, 73%, weight average molecular weight 2,700 daltons) as a white solid.

Example 14

Preparation of Tetrapolymer with Acid Generator Units

A heel solution was made by dissolving 2-phenylpropan-2-yl methacrylate (0.39 g), 2-oxotetrahydrofuran-3-yl methacrylate (0.33 g), 3,5-bis(1,1,1,3,3,3-hexafluoro-2-hydroxypropan-2-yl)cyclohexyl methacrylate (0.57 g) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (0.31 g) in 12.81 g ethyl lactate/gamma butyrolactone (7/3 v/v). Feed solution was prepared by dissolving 2-phenylpropan-2-yl methacrylate (185.54 g, 0.967 mol), 2-oxotetrahydrofuran-3-yl methacrylate (204.27 g, 1.26 mol), 3,5-bis(1,1,1,3,3,3-hexafluoro-2-hydroxypropan-2-yl)cyclohexyl methacrylate (127.98 g, 0.29 mol) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (81.5 g, 0.132 mol) in 606 g ethyl lactate:γ-butyrolactone (30/70 v/v). Initiator solution was prepared by dissolving 65.96 g initiator (2,2'-azobis(2.4-dimethyl valeronitrile)) in 66 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (2.0 g). The contents were cooled to room temperature and precipitated twice out of 10× (by weight) diisopropyl ether/methanol 95/5 (w/w). The polymer obtained was dried under vacuum after each precipitation step at 50° C. for 24 hours to yield 500 g polymer having a weight average molecular weight of 5,200 daltons, a dispersity of 1.5, and a monomer composition of the respective monomers of 36.0 mole percent, 47.5 mole percent, 11.0 mole percent, and 5.5 mole percent.

Example 15

Preparation of Tetrapolymer with Acid Generator Units

The process of Example 14 was repeated, except that equimolar 5-phenyl-5H-dibenzo[b,d]thiophenium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate. The polymer obtained had a weight average molecular weight of 6,300 daltons, a dispersity of 1.4, and respective monomer contents of 36.5 mole percent, 47.5 mole percent, 12.0 mole percent, and 5 mole percent.

Example 16

Preparation of Tetrapolymer with Acid Generator Units

The process of Example 14 was repeated, except that equimolar 5-(4-(tert-butyl)phenyl)-5H-dibenzo[b,d]thiophen-5-ium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d] thiophenium 1,1-difluoro-2-(methacryloyloxy) ethanesulfonate. The polymer obtained had a weight average molecular weight of 5,200 daltons, a dispersity of 1.6, and respective monomer contents of 34 mole percent, 51 mole percent, 9 mole percent, and 6 mole percent.

Example 17

Preparation of Tetrapolymer with Acid Generator Units

The process of Example 14 was repeated, except that an equimolar amount of the monomer of Example 9 was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate. The polymer obtained had a weight average molecular weight of 5,200 daltons, a dispersity of 1.5, and respective monomer contents of 38 mole percent, 46 mole percent, 10 mole percent, and 6 mole percent.

Example 18

Preparation of Tetrapolymer with Acid Generator Units

A heel solution was made by dissolving 2-phenylpropan-2-yl methacrylate (0.53 g), (1S,3R,8S)-5-oxo-4-oxatricyclo[4.3.1.13,8]undecan-1-yl methacrylate (0.44 g), 3,5-bis(1,1,1,3,3,3-hexafluoro-2-hydroxypropan-2-yl)cyclohexyl methacrylate (0.78 g) and phenyldibenzothiophenium 1,1-difluoro-2-(methacryloyloxy)ethanesulfonate (0.42 g) in 20.0 g ethyl lactate/gamma butyrolactone (7/3 v/v). Feed solution was prepared by dissolving 2-phenylpropan-2-yl methacrylate (7.50 g), (1S,3R,8S)-5-oxo-4-oxatricyclo[4.3.1.13,8]undecan-1-yl methacrylate (12.23 g), 3,5-bis(1,1,1,3,3,3-hexafluoro-2-hydroxypropan-2-yl)cyclohexyl methacrylate (4.97 g) and phenyldibenzothiophenium 1,1-difluoro-2-(methacryloyloxy)ethanesulfonate (1.12 g) in 26.0 g ethyl lactate:γ-butyrolactone (3/7 v/v). Initiator solution was prepared by dissolving 2.59 g initiator (2,2'-azobis (2.4-dimethyl valeronitrile)) in 2.59 g acetonitrile/tetrahydrofuran (2/1 v/v). The polymerization was carried out in a 200 mL 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (0.200 g). The contents were cooled to room temperature and precipitated twice out of 10× (by weight) diisopropyl ether/methanol 95/5 (w/w). The polymer obtained was dried under vacuum after each precipitation step at 50° C. for 24 hours to yield 26 grams of polymer having a weight average molecular weight of 5,000 daltons, a dispersity of 1.5, and respective monomer contents of 36 mole percent, 47 mole percent, 12 mole percent, and 5 mole percent.

Example 19

Preparation and Processing of a Photoresist Composition

Non-polymeric photoacid generators and photo-destroyable quenchers (collectively, "additives") used in the preparation of photoresist compositions are summarized in Table 1. Photoresist compositions are summarized in Table 2. The Example 19 positive-tone photoresist composition was prepared by combining component 1, 5.33 g of a 10 weight percent solution of the polymer of Example 17 in ethyl lactate; component 2, 10.373 g of a 2 weight percent solution of the additive A-1 in ethyl lactate; component 3, 0.320 g of a 0.5 weight percent solution of tetrakis(2-hydroxypropyl)ethylenediamine in ethyl lactate; component 4, 0.356 g of a 2 weight percent solution of the additive A-2 in ethyl lactate; component 5, 0.107 g of a 0.5 weight percent solution of fluorinated surfactant (Omnova PF656) in ethyl lactate; component 6, 4.737 g of ethyl lactate; and component 7, 8.775 g of 2-hydroxyisobutyric acid methyl ester. The formulated resist was passed through a 0.01 micrometer (μm) polytetrafluoroethylene (PTFE) filter. The thus prepared resist was spin coated onto a silicon wafer, soft baked to remove carrier solvent and exposed through a photomask to EUV radiation. The imaged resist layer was then baked at 110° C. for 60 seconds and then developed with an aqueous alkaline composition.

TABLE 1

| Additive | Structure |
|---|---|
| A-1 | 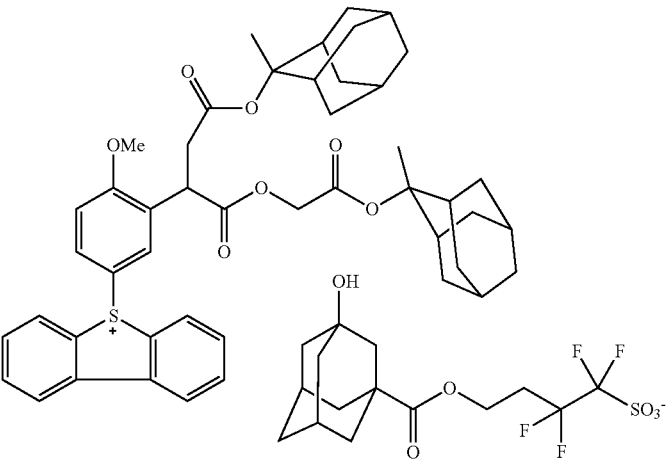 |
| A-2 | 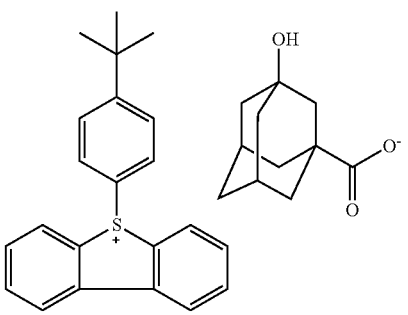 [SMILES: CC(C)(C)c1ccc(-[s+]2c3ccccc3c3ccccc32)cc1 ; O=C([O-])C12CC3CC(CC(O)(C3)C1)C2] |

TABLE 1-continued

| Additive | Structure |
|---|---|
| A-3 | (structure shown) |
| A-4 | (structure shown) |

For Table 2, below, components 1-7 correspond to the descriptions in Example 19. Component amounts, in brackets, are expressed in units of grams.

TABLE 2

| Ex. | Comp. 1 (polymer) | Comp. 2 (PAG) | Comp. 3 (quencher) | Comp. 4 (PDQ) | Comp. 5 (surfactant) | Comp. 6 (solvent) | Comp. 7 (solvent) |
|---|---|---|---|---|---|---|---|
| 19 (C) | Ex. 17 [5.33] | A-1 [10.37] | [0.320] | A-2 [0.356] | [0.107] | [4.737] | [8.775] |
| 20 (C) | Ex. 16 [9.378] | A-1 [14.79] | [0.563] | A-2 [0.626] | [0.188] | [9.826] | [14.63] |
| 21 (C) | Ex. 18 [8.229] | — | [0.247] | — | [0.165] | [26.61] | [14.75] |
| 22 (C) | Ex. 14 [55.43] | A-3 [94.24] | [13.31] | — | [1.109] | [48.17] | [87.75] |
| 23 (I) | Ex. 9 [0.987]* | — | [2.467] | — | [0.197] | [24.64] | [11.70] |
| 24 (I) | Ex. 10 [0.205]* | — | [0.513] | — | [0.041] | [4.903] | [2.388] |
| 25 (I) | Ex. 11 [0.247]* | — | [0.617] | — | [0.049] | [6.162] | [2.925] |
| 26 (I) | Ex. 12 [0.247]* | — | [0.617] | — | [0.049] | [6.162] | [2.925] |
| 27 (I) | Ex. 11 [15.64]** | — | [0.704] | Ex. 1 [4.543]*** | [0.235] | [21.25] | [17.64] |
| 28 (I) | Ex. 12 [15.64] | — | [0.938] | Ex. 1 [6.057]*** | [0.313] | [33.54] | [23.52] |
| 29 (I) | Ex. 13 [15.64] | — | [0.938] | Ex. 1 [6.057]*** | [0.313] | [33.54] | [23.52] |
| 30 (C) | Ex. 16 [7.867] | A-4 [9.745] | [0.472] | Ex. 1 [0.762]*** | [0.157] | [9.296] | [11.70] |

TABLE 2-continued

| Ex. | Comp. 1 (polymer) | Comp. 2 (PAG) | Comp. 3 (quencher) | Comp. 4 (PDQ) | Comp. 5 (surfactant) | Comp. 6 (solvent) | Comp. 7 (solvent) |
|---|---|---|---|---|---|---|---|
| 31 (C) | Ex. 15 [15.92] | — | [0.478] | — | [0.318] | [25.76] | [17.52] |

*Added as solid.
**Added as 7.50 weight percent solution in ethyl lactate.
***Added as 0.5 weight percent in ethyl lactate.

Critical Dimension Uniformity.

Critical dimension uniformity (CDU) is the calculated 3 Sigma (three standard deviations) for ten Fields of View (FOV) measuring 36 contact holes for each FOV, all taken at Best Exposure/Best Focus at 30 nm contact hole resolution with 1:1 half pitch. Each data point has been pre-normalized to a standard EUV photoresist which is run in each lithographic slot to eliminate variability and noise. The results, presented in Table 3, show that the lowest (best) CDU value is exhibited by the inventive Example 23 photoresist. In Table 3, the CDU of Example 23 is normalized to 1, and designated with "◊". Comparative examples which underperform relative to the example by 0-5% are designated with "●"; comparative examples which underperform relative to the example by 5%-15% are designated with "■"; and comparative examples which underperform relative to the example by >15% are designated with "☐". In Table 3, "PolyPAG" refers to a polymer comprising 50 to 100 mole percent of photoacid-generating repeat units, "Polymer-bound-PAG" refers to a polymer comprising photoacid-generating repeat units in an amount less than 50 mole percent, and "free PAG" refers to a non-polymer-bound photoacid-generator.

TABLE 3

| Example | PAG Type | Relative CDU |
|---|---|---|
| Example 23 | PolyPAG | ◊ |
| Comparative Example 19 | Polymer-bound-PAG + free PAG | ☐ |
| Comparative Example 31 | Polymer-bound-PAG | ☐ |
| Comparative Example 22 | Polymer-bound-PAG + free PAG | ☐ |
| Comparative Example 20 | Polymer-bound-PAG + free PAG | ■ |

Dose to Clear.

Extreme ultraviolet (EUV) dose to clear was measured as the dose at 5% remaining film thickness. Data was collected either on a Litho Tech Japan (LTJ) EVUES-9000 tool or on the Albany MET tool at the College of Nanoscale Science and Technology at the State University of New York, Albany. Processing conditions were a soft bake at 110° C. for 90 seconds, a post exposure bake for at 100° C. for 60 seconds, and development for 30 seconds at room temperature in 0.26 N tetramethylammonium hydroxide developer.

Dose to clear results are summarized in Table 4. Dose to clear values for inventive Examples 23-26 are normalized to a value of 1.00 for Comparative Example 21. Values below 1.00 represent a desirable decrease in dose to clear energy. The results show that inventive photoresist compositions 23-26 exhibit substantially decreased dose to clear energies relative to the Example 21 comparison. The results are consistent with the hypothesis that a progression from polymer-bound-PAG to (polymer-bound-PAG+additive PAG) to polyPAG will result in an increased sensitivity due to PAG density and uniformity.

TABLE 4

| Example | PAG Type | Normalized $E_0$ |
|---|---|---|
| Comparative Example 21 | Polymer-bound-PAG | 1.00 |
| Example 23 | PolyPAG | 0.69 |
| Example 24 | PolyPAG | 0.64 |
| Example 25 | PolyPAG | 0.61 |
| Example 26 | PolyPAG | 0.54 |

In Table 5, inventive Examples 27-29 are normalized to a value of 1.00 for Comparative Example 31. Values below 1.00 represent a desirable decrease in dose to clear energy. The results show that inventive photoresist compositions 27-29 exhibit decreased dose to clear energies relative to the Example 31 comparison. The results are again consistent with the hypothesis that a progression from polymer-bound-PAG to polyPAG will result in an increased sensitivity due to PAG density and uniformity.

TABLE 5

| Example | PAG Type | Normalized $E_0$ |
|---|---|---|
| Comparative Example 31 | Polymer-bound-PAG | 1.00 |
| Example 27 | PolyPAG | 0.83 |
| Example 28 | PolyPAG | 0.69 |
| Example 29 | PolyPAG | 0.97 |

Contrast Slope.

EUV contrast slope was measured as the slope of the contrast curve between 95% and 5% film thickness during positive tone development. Data was collected either on a Litho Tech Japan (LTJ) EVUES-9000 tool or on the Albany MET tool at the College of Nanoscale Science and Technology at the State University of New York, Albany. Processing conditions were a soft bake at 110° C. for 90 seconds, a post-exposure bake for at 100° C. for 60 seconds, and development for 30 seconds at room temperature in 0.26 N tetramethylammonium hydroxide developer. In Table 6 the contrast slope of Comparative Example 30 was normalized to 1.00, and designated with "◊". Inventive examples that outperform relative to the comparative example by 10%-20% are designated with "■"; and inventive examples that outperform relative to the comparative example by >20% are designated with "☐". The results show that for the property of contrast slope, inventive Example 27 outperforms Comparative Example 30 by at least 10%, and inventive Examples 28 and 29 outperform Comparative Example 30 by at least 20%.

TABLE 6

| Examples | PAG Type | Relative Contrast Slope |
|---|---|---|
| Comparative Example 30 | Polymer-bound-PAG + free PAG | ◊ |

TABLE 6-continued

| Examples | PAG Type | Relative Contrast Slope |
|---|---|---|
| Example 27 | PolyPAG | ■ |
| Example 28 | PolyPAG | □ |
| Example 29 | PolyPAG | □ |

In Table 7, the contrast slope of Comparative Example 19 was normalized to 1, and designated with "◊". Inventive examples that outperform the comparative example by >20% are designated with "□". The results show that for the property of contrast slope, inventive Example 23-26 outperform Comparative Example 21 by at least 20%. The results are consistent with the hypothesis that a progression from polymer-bound-PAG to polyPAG will result in greater (more negative) contrast slope.

TABLE 7

| Example | PAG Type | Relative Contrast Slope |
|---|---|---|
| Comparative Example 21 | Polymer-bound-PAG | ◊ |
| Example 23 | PolyPAG | □ |
| Example 24 | PolyPAG | □ |
| Example 25 | PolyPAG | □ |
| Example 26 | PolyPAG | □ |

The invention claimed is:

1. A polymer comprising, based on 100 mole percent of total repeat units, 60 to 100 mole percent of photoacid-generating repeat units, wherein each of the photoacid-generating repeat units comprises (a) photoacid-generating functionality and (b) base-solubility-enhancing functionality selected from the group consisting of tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha,beta-fluorinated esters, polyalkyleneglycols, alpha-fluorinated alcohols, and combinations thereof:

wherein the photoacid-generating repeat units have the structure

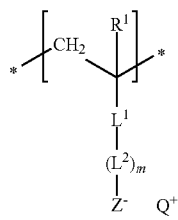

wherein $R^1$ is independently in each of the repeat units H, F, —CN, $C_{1-10}$ alkyl, or $C_{1-10}$ fluoroalkyl;

$L^1$ is independently in each of the repeat units —O—, —C(O)—O—, unsubstituted $C_{6-18}$ arylene, or substituted $C_{6-18}$ arylene;

m is independently in each of the repeat units 0 or 1;

$L^2$ is independently in each of the repeat units an unsubstituted or substituted $C_{1-20}$ hydrocarbylene, wherein the substituted $C_{1-20}$ hydrocarbylene can, optionally, include one or more in-chain divalent heteroatom-containing groups that is —O—, —S—, —NR²—, —PR²—, —C(O)—, —OC(O)O—, —N(R²)C(O)—, —C(O)N(R²)—, —OC(O)N(R²)—, —N(R²)C(O)O—, —S(O)—, —S(O)₂—, —N(R²)S(O)₂—, —S(O)₂N(R²)—, —OS(O)₂—, or —S(O)₂O—, wherein R² is H or $C_{1-12}$ hydrocarbyl;

$Z^-$ is independently in each of the repeat units sulfonate (—SO₃⁻), sulfonamidate, which is an anion of sulfonamide, —S(O)₂N—R³, wherein R³ is H or unsubstituted or substituted C1-12 hydrocarbyl, or sulfonimidate, which is an anion of sulfonamide, —S(O)₂N⁻S(O)₂R³, wherein R³ is H or unsubstituted or substituted C1-12 hydrocarbyl; and $Q^+$ is photoacid-generating cation;

wherein at least one of $L^1$, $L^2$ (when m is 1), and $Q^+$ comprises the base-solubility-enhancing functionality.

2. The polymer of claim 1, comprising 95 to 100 mole percent of the photoacid-generating repeat units.

3. The polymer of claim 1, wherein the photoacid-generating repeat units are derived from a single monomer.

4. The polymer of claim 1, wherein the photoacid-generating repeat units are derived from at least two different monomers.

5. The polymer of claim 1, wherein the base-solubility-enhancing functionality is a tertiary carboxylic acid ester, an acetal, a ketal, a lactone, or a combination thereof.

6. A photoresist composition comprising the polymer of claim 1 and a solvent.

7. A method of forming an electronic device, comprising:
(a) applying a layer of the photoresist composition of claim 6 on a substrate;
(b) pattern-wise exposing the photoresist composition layer to activating radiation; and
(c) developing the exposed photoresist composition layer to provide a resist relief image.

* * * * *